United States Patent
Saada

(10) Patent No.: US 10,366,619 B2
(45) Date of Patent: Jul. 30, 2019

(54) LEARNING AND ADVANCEMENT SYSTEM AND METHOD THEREOF

(71) Applicant: Jerry Yaacov Saada, Jerusalem (IL)

(72) Inventor: Jerry Yaacov Saada, Jerusalem (IL)

(*) Notice: Subject to any disclaimer, the term of this patent is extended or adjusted under 35 U.S.C. 154(b) by 0 days.

(21) Appl. No.: 15/102,379

(22) PCT Filed: Dec. 1, 2014

(86) PCT No.: PCT/IL2014/051040
§ 371 (c)(1),
(2) Date: Jun. 7, 2016

(87) PCT Pub. No.: WO2015/087318
PCT Pub. Date: Jun. 18, 2015

(65) Prior Publication Data
US 2016/0314698 A1    Oct. 27, 2016

(30) Foreign Application Priority Data

Dec. 9, 2013 (IL) .......................................... 229868

(51) Int. Cl.
*G09B 5/00* (2006.01)
*G09B 5/06* (2006.01)
(Continued)

(52) U.S. Cl.
CPC ............ *G09B 5/065* (2013.01); *A61M 21/02* (2013.01); *G09B 5/06* (2013.01); *G09B 19/00* (2013.01);
(Continued)

(58) Field of Classification Search
CPC .......... G09B 5/06; G09B 5/065; A61M 21/02; A61B 5/16; A61B 5/165
(Continued)

(56) References Cited

U.S. PATENT DOCUMENTS 5,304,112 A * 4/1994 Mrklas .............. A61M 21/0094
434/236
5,586,967 A * 12/1996 Davis .................... A61M 21/00
600/28
(Continued)

FOREIGN PATENT DOCUMENTS

CN    101976514 A    2/2011
ES    1 078 739 U    2/2013

OTHER PUBLICATIONS

Patent Cooperation Treaty, International Search Report, International Patent Application No. PCT/IL2014/051040, dated Mar. 26, 2015, 3 Pages.
(Continued)

*Primary Examiner* — Peter R Egloff
(74) *Attorney, Agent, or Firm* — Fenwick & West LLP

(57) ABSTRACT

The present invention relates to a learning and advancement system in form of an audiovisual stimulator device that is configured to stimulate a user's brain to induce various brain wave frequencies, comprising: a) a timing module for defining a breathing sequence timing to be displayed to the user, wherein said breathing sequence includes inspiration timing, exhalation timing and hold breath timing; and b) a processing unit adapted to control visual and audible signals to display and play learning content according to the timing of said breathing sequence.

12 Claims, 1 Drawing Sheet

(51) Int. Cl.
   *A61M 21/02* (2006.01)
   *G09B 19/00* (2006.01)
   *A61M 21/00* (2006.01)

(52) U.S. Cl.
   CPC .............. *A61M 2021/0027* (2013.01); *A61M 2021/0044* (2013.01); *A61M 2021/0088* (2013.01)

(58) Field of Classification Search
   USPC ........................................................ 434/236
   See application file for complete search history.

(56) References Cited

U.S. PATENT DOCUMENTS

| | | | | |
|---|---|---|---|---|
| 6,425,764 | B1* | 7/2002 | Lamson | A61M 21/00 434/236 |
| 7,507,206 | B2* | 3/2009 | Graves | A61B 5/486 600/26 |
| 2003/0194684 | A1* | 10/2003 | LaBrosse | G09B 19/00 434/236 |
| 2005/0124906 | A1* | 6/2005 | Childre | A61B 5/02405 600/529 |
| 2008/0269629 | A1 | 10/2008 | Reiner | |
| 2011/0004047 | A1* | 1/2011 | Braspenning | A61B 5/02405 600/27 |
| 2011/0066005 | A1* | 3/2011 | Rotenberg | A61B 5/02405 600/301 |
| 2011/0306024 | A1* | 12/2011 | Furuta | G09B 19/00 434/258 |
| 2013/0177883 | A1* | 7/2013 | Barnehama | G09B 5/00 434/236 |

OTHER PUBLICATIONS

Patent Cooperation Treaty, Written Opinion of the International Searching Authority, International Patent Application No. PCT/IL2014/051040, dated Mar. 26, 2015, 5 Pages.

Patent Cooperation Treaty, International Preliminary Report on Patentability, International Patent Application No. PCT/IL2014/051040, dated Feb. 2, 2016, 11 Pages.

European Extended Search Report, European Application No. 14870430.7, dated Aug. 10, 2017, 11 pages.

* cited by examiner

LEARNING AND ADVANCEMENT SYSTEM AND METHOD THEREOF

FIELD OF THE INVENTION

The present invention relates to the field of learning systems. More particularly, the invention relates to a therapeutic method and system for improving cognitive skills such as memory and learning.

BACKGROUND OF THE INVENTION

In recent years, one cerebral rhythm has attracted particular attention: the alpha rhythm. Physicians, psychologists, and teachers are concentrating on these waves. They credit alpha waves with the power of improving the ability to rapidly learn, absorb, and memorize information.

Many neurophysiologists, ElectroEncephaloGraphists (EEG technicians), and clinicians involved in brain science have come to understand that the most gifted learners are able to easily produce alpha waves. A study conducted on Einstein's brain showed that he was very frequently in alpha state. Even while he was performing rather difficult calculations his EEG showed no arrest reaction, no reflexive pause. A study regarding cerebral activity in children shows that they are very productive of alpha waves till adolescence—thus their great ability to absorb new material. The beta rhythm predominates afterward, and during adulthood.

It is an object of the present invention to provide a system which is capable of guiding a user to breathe effectively during a learning process.

It is another object of the present invention to provide a system which is capable of inducing various brain wave frequencies, in particular during a learning process.

Other objects and advantages of the invention will become apparent as the description proceeds.

SUMMARY OF THE INVENTION

The present invention relates to a learning and advancement system in form of an audiovisual stimulator device that is configured to stimulate a user's brain to induce various brain wave frequencies, comprising: a) a timing module for defining a breathing sequence timing to be displayed to the user, wherein said breathing sequence includes inspiration timing, exhalation timing and hold breath timing; and b) a processing unit adapted to control visual and audible signals to display and play learning content according to the timing of said breathing sequence.

According to an embodiment of the invention, the device further comprises a display for displaying the learning content and the breathing sequence.

According to an embodiment of the invention, the device further comprises a subliminal module for generating subliminal sound(s) or image(s) during the inspiration and exhalation timing of the breathing sequence.

According to an embodiment of the invention, the device further comprises at least one speaker (e.g., an earphone) for outputting the audible signals.

According to an embodiment of the invention, the device is configured in form of a wearable computer based device, in particular video glasses.

In another aspect, the present invention relates to a method for stimulating a user's brain to induce various brain wave frequencies, comprising: a) defining a breathing sequence timing to be displayed to the user, wherein said breathing sequence includes inspiration timing, exhalation timing and hold breath timing; and b) providing visual and audible signals for displaying and playing learning content according to the timing of said defined breathing sequence.

According to an embodiment of the invention, further comprises generating subliminal sound(s) and/or visual image(s) during the inspiration and exhalation timing of the breathing sequence for enhancing the ability of the user to memorize the learning content.

According to an embodiment of the invention, the inspiration timing and the exhalation timing are visualized on a display by at least one moveable object that accordingly reflects the tasks of inspiration and exhalation.

According to an embodiment of the invention, the timing of the breathing sequence is defined by inspiration of 2 seconds, expirations of 2 seconds, and hold breath timing of 4 seconds.

DETAILED DESCRIPTION OF THE INVENTION

The present invention relates to an audiovisual stimulator device that is configured to stimulate a user's brain to induce various brain wave frequencies in synchronization with optimal breathing sequence. The device integrates video programs in a pattern of combined rhythmic stimulations consisting of binaural and luminous signals that encourage the brain zones associated with memorization.

Reference will now be made to several embodiments of the present invention, examples of which are illustrated in the accompanying figures.

Wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

The sequence of the stimuli presented by the method utilized in the present disclosure follows and supports the process of learning and higher cognitive function. It has been discovered that, if the correct timing frequency of breath cycle is used in conjunction with brain waves generation such as alpha and theta, the subject's brain will respond accordingly, attempting to match the frequency of visual learning content by a sympathetic brain wave output and thereby providing an enhanced memory result.

Because the invention has the capability to varying the frequency of stimuli generation across a broad range, any of desired brain states can be achieved for advanced learning. Of particular interest is the alpha state however, as this represents the level of brain activity most conducive to learning and which can take full advantage of the invention's unique characteristics. The connection between learning and the alpha state has been described in Superlearning, Ostrander, et al, Delacarte, New York, N.Y. (1979). The individual using the invention, according to a specific guideline breath timing sequence, becomes quickly accustomed to the desired breath sequence. Thus activities such as learning languages, listening to tapes, lectures and the like are carried out in a hyper-attentive state. Attaining the alpha state may also be desirable simply for purposes of relaxation rather than learning per se. A meditative state may be obtained. The term superlearning refers to an eclectic system for accelerated learning of factual data resulting from westernized, modernized techniques for developing supermemory, such as the novel device of the present invention.

In similar fashion, theta and delta states are initiated by continuing the frequency of stimuli generation as outlined above. The subject is most advantageously in a supportive position such as lying down on a couch or bed, or reclining in a chair.

Figure 1:
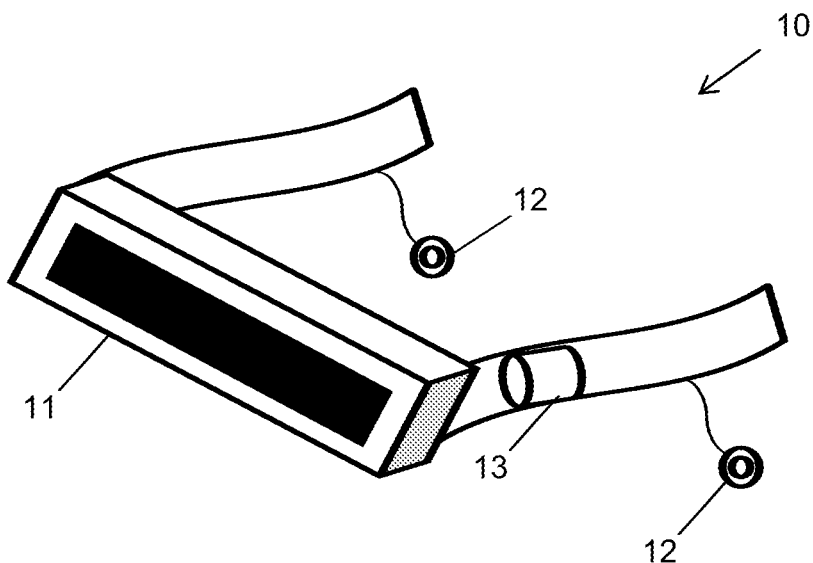
FIG. 1 schematically illustrates an implementation of an audiovisual stimulator device, according to an embodiment of the invention.

FIG. 1 shows an audiovisual stimulator device that can be used in conjunction with the invention. The device illustrated in this figure is particularly convenient because it is configured in form of a wearable computer based device, video glasses or a head mounted display. The device generally indicated by numeral 10 in the figure comprises a display 11, one or more speakers 12 and a processing unit 13.

Figures 2A, 2B, 2C:
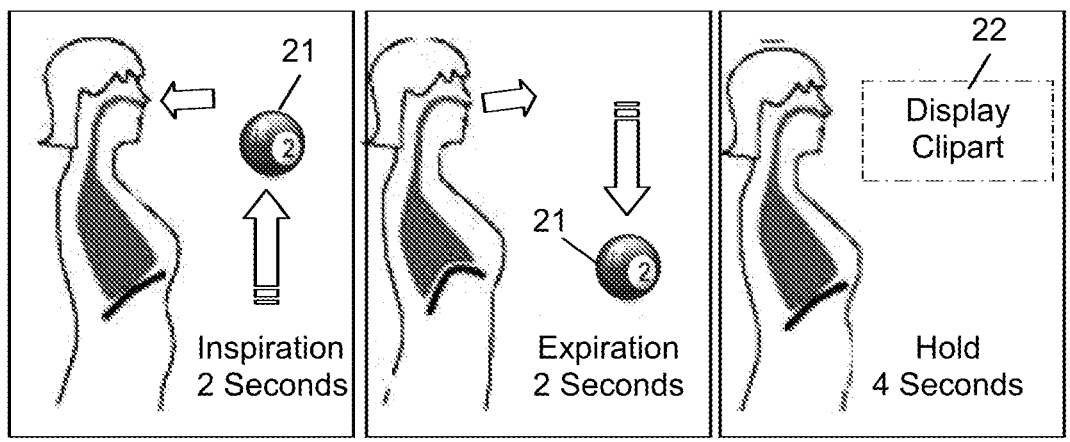
FIGS. 2A-2C schematically illustrate an exemplary visual breathing sequence guideline, according to an embodiment of the invention.

The processing unit 13 has a variety of functions. Foremost a breathing rhythm function is provided. The breathing sequence is shown on the display 11. An optional rhythm control option may allow selecting a fixed rhythm or alternative breathing sequences. A preferred breathing sequence is shown in FIGS. 2A-2C.

The device 10 is characterized in that it comprises an abdominal breathing guide that instructs the user when the inspiration finish and expiration start. The processing unit 13 controls visual and audible signals to display and play the learning content according to the inspiration finish and expiration start. According to the abdominal breathing sequence, the device 10 controls the playing and displaying of the learning contents in form of voice message, images (e.g., pictures and clipart), text messages, and the gentle dives brain music is mixed and circularly played, so that the user can easily make the brain fill with alpha brain wave and maintain the high relaxed alert condition during the whole learning and memory process.

Following the visual guideline breathing sequence (see FIGS. 2A-2C), the user is able to breathe according to the desired abdominal respiration sequence that is synchronized with the playing and the displaying of the learning contents of speech information and image-text information. In addition, a tender and slow music is played in a circular and mixed way, so that the user can be entered into a relaxed state through the learning and memorizing processes, as the brain filled with alpha waves and in a high relaxed alertness state, thus the learning efficiency and the learning effect are improved.

According to an embodiment of the invention, device 10 further comprises generating subliminal sound(s) and/or visual image(s) during the inspiration and exhalation timing of the breathing sequence for enhancing the ability of the user to memorize the learning content. For example, a subliminal module can be used for generating the subliminal sound(s) or image(s) during the inspiration and exhalation timing of the breathing sequence.

Traditional instruction turns out to be based on the hemisphere (logical analysis, rationality, critical consideration, etc.) and neglects the right brain hemisphere (images, creativity, emotions, and dreams). According to an embodiment of the invention, in order to increase the brain's abilities of a user, the device 10 can be configured to work on activating both hemispheres with changing audible (e.g., sounds) and visual (e.g., lights) frequencies. This allows for relaxation, increased creativity, and readiness for sleep or conversely alertness, depending on the frequencies used in the chosen pre-defined program. For example, device 10 can be configured to work according to techniques such as those suggested by Dr. Gerald Oster, of the Mount Sinai School of Medicine in New York. These techniques employ various sound frequencies for each of the ears, allowing for the induction of low-frequency brain waves such as are observed in states of meditation, and for achieving perfect synchronization of the two brain hemispheres—a favorable condition for change in general.

Device 10 may include variety of brain wave programs, that may consists purely of stereophonic sound, rhythmic sounds (with no voice or melody) and stroboscopic images adapted to enable the user's mind to rest, relax and recuperate.

Referring now to FIGS. 2A-2C, an exemplary visual representation of a breathing sequence is shown, in accordance with an embodiment of the invention. In this example, the display 11 of device 10 shows to the user a visual effect that reflects the breathing process, e.g., in form of a ball 21 the goes up during the inhalation (FIG. 2A) and goes down during the exhalation (FIG. 2B). The inspiration timing and the exhalation timing can be visualized on a display by at least one moveable object (such as the ball 21) that accordingly reflects the tasks of inspiration and exhalation. As will be apparent to a skilled person, other visual effects can be used to reflect the berating sequence, such as a visual effect of an approaching and receding object.

The entire breathing sequence is completed by guiding the user to hold the breath for a short time (e.g., 4 seconds) during which a learning content is shown to the user (as indicated by numeral 22 in FIG. 2C). The timing of the breathing process can be set according to known methods, such as the Lozanov method which focuses on two distinct rhythms of breathing. The preparatory breathing: inhale for four seconds, four seconds of pause, then exhale for four seconds, and then again four seconds pause. Breathing during learning: inhale for two seconds, exhale for two seconds and four seconds pause. It is assumed that during the hold phase (e.g., 4 seconds) between expiration and inspiration, it is the preferred timing of memorizing/learning the display content.

Using device 10, the user may act as follows:

When the ball 21 goes up, the user should begin the inspiration process for 2 seconds, and when the ball 21 goes down the user should begin the expiration process for 2 seconds, after that the user should hold the breath for 4 seconds and watch the clip that is presented during that time on the display of device 10.

The following discussion intended to provide a brief, general description of a suitable computing environment in which the invention may be implemented. While the invention is described in the general context of program modules that execute in conjunction with an application program that runs on an operating system on a wearable computer based device, those skilled in the art will recognize that the invention may also be implemented in combination with other program modules on other computer based systems or device.

Embodiments of the invention may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be received in a propagated signal on a carrier wave readable by a computing system and encoding a computer program of instructions for executing a computer process.

Unless otherwise indicated, the functions described herein may be performed by executable code and instructions stored in computer readable medium and running on one or more processor-based systems. However, state machines, and/or hardwired electronic circuits can also be utilized. Further, with respect to the example processes described herein, not all the process states need to be reached, nor do the states have to be performed in the illustrated order. Further, certain process states that are illustrated as being serially performed can be performed in parallel.

Similarly, while certain examples may refer to a wearable computer based device, other computer or electronic systems can be used as well, such as, without limitation, a Personal Computer (PC), a tablet, an interactive television, a network-enabled personal digital assistant (PDA), a network game console, a networked entertainment device, a smart phone (e.g., with an operating system and on which a user can install applications) and so on.

As will be appreciated by the skilled person the arrangement described in the figures results in a learning and advanced system which is capable of guiding a user to breathe effectively during a learning process, and which is capable of inducing various brain wave frequencies, in particular during that learning process All the above description and examples have been given for the purpose of illustration and are not intended to limit the invention in any way. Many different mechanisms, methods of analysis, electronic and logical elements can be employed, all without exceeding the scope of the invention.

The invention claimed is:

1. A wearable computer-based device, comprising:
   a) an audiovisual signal generator that is configured to generate visual and binaural audible signals at one or more predetermined frequencies, the signal frequencies suitable for inducing desired brain wave frequencies for stimulating a user's brain;
   b) a memory module in which learning content and information related to a guideline breathing sequence are stored;
   c) a player for presenting said stored learning content and information;
   d) a timing module configured to retrieve said stored information and to define breathing sequence timing to be displayed to a user, wherein said breathing sequence includes an inspiration phase, an expiration phase, and a hold phase; and
   e) a processing unit, adapted to synchronize said visual and binaural audible signals and the playing of said learning content with said breathing sequence, wherein the learning content is displayed to the user during the hold phase.

2. The device according to claim 1, wherein the player includes a display on which the learning content and visual effects indicative of the breathing sequence are displayable.

3. The device according to claim 1, wherein the signal generator is a subliminal signal generator for playing one or more subliminal sounds or images during the inspiration and exhalation phases of the breathing sequence.

4. The device according to claim 1, wherein the player comprises at least one speaker for outputting audible signals suitable for inducing desired brain wave frequencies and for outputting audible learning content and information related to the breathing sequence.

5. The device according to claim 4, wherein the at least one speaker is part of an earphone.

6. The device according to claim 1, wherein the information related to the breathing sequence is indicated by visual effects that instruct the user when inspiration and exhalation operations should be performed.

7. The device according to claim 1, wherein the device comprises video glasses or a head mounted display.

8. The device according to claim 1, wherein the visual or audible signals include stereophonic sound, rhythmic sounds, or stroboscopic images.

9. A method for enhancing learning and memory, comprising:
   generating, by the audiovisual signal generator of the wearable device of claim 1, visual and binaural audible signals at one or more predetermined frequencies suitable for inducing alpha brain wave frequencies;
   by the timing module, instructing a user to breathe according to the breathing sequence;
   by the player, playing stored learning content; and
   by the processing unit, synchronizing said visual and binaural audible signals and said learning content to play during the hold phase of said breathing sequence.

10. The method according to claim 9, further comprising playing subliminal sound(s) and/or displaying visual image(s) during the inspiration and exhalation phases of the breathing sequence.

11. The method according to claim 9, wherein the breathing sequence is visualized on a display by at least one moveable object.

12. The method according to claim 9, wherein timing of the breathing sequence is defined by an inspiration phase of 2 seconds, an expiration phase of 2 seconds, and a hold phase of 4 seconds.

* * * * *